United States Patent [19]

Arnold et al.

[11] Patent Number: 5,081,256
[45] Date of Patent: Jan. 14, 1992

[54] PARA ORDERED AROMATIC DIACIDS CONTAINING BENZIMIDAZOLE GROUPS

[75] Inventors: Fred E. Arnold; Loon-Seng Tan, both of Centerville, Ohio

[73] Assignee: United States of America as represented by the Secretary of the Air Force, Washington, D.C.

[21] Appl. No.: 686,203

[22] Filed: Apr. 16, 1991

[51] Int. Cl.$^5$ .................. C07D 235/18; C07D 403/02; C07D 417/02
[52] U.S. Cl. .................................. 548/159; 548/328; 548/334
[58] Field of Search ........................ 548/159, 328, 334

[56] References Cited

U.S. PATENT DOCUMENTS 4,892,921 1/1990 Tsai et al. ............................ 528/183
4,892,953 1/1990 Arnold et al. ....................... 548/156

Primary Examiner—Mary C. Lee
Assistant Examiner—Lenora Miltenberger
Attorney, Agent, or Firm—Charles E. Bricker; Donald J. Singer

[57] ABSTRACT

2-Benzimidazole terephthalic acid, 4,4'-dicarboxy-2,2'-bisbenzimidazole biphenyl and 4,4''-dicarboxy-2'-phenyl-3'-[2-(4-phenylbenzthiazole)]-6'-[2-(3-phenylbenzimidazole]-p-terphenyl are provided.

Also provided are methods for preparing these dicarboxylic acids. 2-benzimidazole terephthalic acid is prepared by reacting trimellitic anhydride with o-phenylenediamine in a suitable solvent. 4,4'-dicarboxy-2,2'-bisbenzimidazole biphenyl is prepared by diazotizing 2-amino-5-bromobenzoic acid to prepare 4,4'-dibromodiphenic acid, reacting the 4,4'-dibromodiphenic acid with o-phenylenediamine in trimethylsilyl polyphosphate solution to prepare 4,4'-dibromo-2,2'-bisbenzimidazolyl biphenyl, reacting the 4,4'-dibromo-2,2'-bisbenzimidazolyl biphenyl with cuprous cyanide to prepare the corresponding dicyano compound, and hydrolyzing the dicyano compound. 4,4''-Dicarboxy-2'-phenyl-3'-[2-(4-phenylbenzthiazole)]-6'-[2-(3-phenylbenzimidazole)]-p-terphenyl is prepared by reacting a 4-benzazole benzil with 1,3-bis(p-bromophenyl)-2-propanone to prepare 2,5-bis(p-bromophenyl)-3-phenyl-4-(2-phenylbenzazole) cyclopentadienone, reacting the cyclopentadienone with 2-(3-ethynylphenyl) benzimidazole to prepare the corresponding dibromo terphenyl compound, reacting the dibromo terphenyl compound with cuprous cyanide to prepare the corresponding dicyano terphenyl compound, and hydrolyzing the dicyano compound.

3 Claims, No Drawings

PARA ORDERED AROMATIC DIACIDS CONTAINING BENZIMIDAZOLE GROUPS

RIGHTS OF THE GOVERNMENT

The invention described herein may be manufactured and used by or for the Government of the United States for all governmental purposes without the payment of any royalty.

BACKGROUND OF THE INVENTION

This invention relates to para ordered aromatic dicarboxylic acids containing benzimidazole groups.

In general, the class of aromatic heterocyclic extended chain polymers are well known for their outstanding thermal, physical and chemical properties. These polymers generally exhibit excellent modulus and tenacity properties.

Tsai et al, U.S. Pat. No. 4,892,921, disclose that the aromatic heterocyclic extended chain polymers lack good properties when in compression. Tsai et al disclose para-ordered aromatic heterocyclic extended chain polymers having pendant benzoxazole and benzothiazole groups which have good properties when in compression.

Arnold et al, U.S. Pat. No. 4,892,953, disclose phenylbenzthiazole-substituted diacid terphenyl monomers which are used for making aromatic heterocyclic extended chain polymers which exhibit improved compressive properties.

We have prepared new para-ordered aromatic diacids containing benzimidazole groups. Benzimidazole-pendant polymers prepared from these diacids, when treated with phosphoric acid, form stable benzimidazonium cations. The acid treated polymers exhibit improved thermooxidative stability as compared to alkaline treated polymers.

Accordingly, it is an object of the present invention to provide novel para-ordered aromatic diacids containing benzimidazole groups.

It is another object of the present invention to provide methods for preparing these para-ordered aromatic diacids containing benzimidazole groups.

Other objects, aspects and advantages of the present invention will become apparent to those skilled in the art from a reading of the following detailed description of the invention.

SUMMARY OF THE INVENTION

In accordance with the present invention, there are provided 2-benzimidazole terephthalic acid, 4,4'-dicarboxy 2,2'-bisbenzimidazole biphenyl and 4,4''-dicarboxy-2'-phenyl-3'-[2-(4-phenylbenzthiazole)]-6'-[2-(3-phenylbenzimidazole)]-p-terphenyl.

Also provided are methods for preparing these diacids.

DESCRIPTION OF THE PREFERRED EMBODIMENTS

2-Benzimidazole terephthalic acid is prepared as illustrated by the following equation:

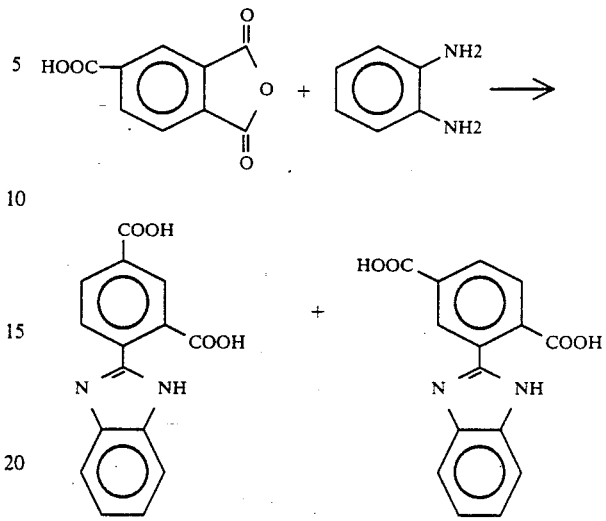

As shown by the equation above, trimellitic anhydride is reacted with o-phenylenediamine to form 2-benzimidazole terephthalic acid and 4-benzimidazole isophthalic acid. The reaction is carried out in a suitable solvent such as DMF, at a suitable temperature, such as at reflux of the solvent. Upon cooling, the desired 2-benzimidazole terephthalic acid precipitates from solution.

4,4'-Dicarboxy-2,2'-bisbenzimidazole biphenyl is prepared as illustrated by the following equations:

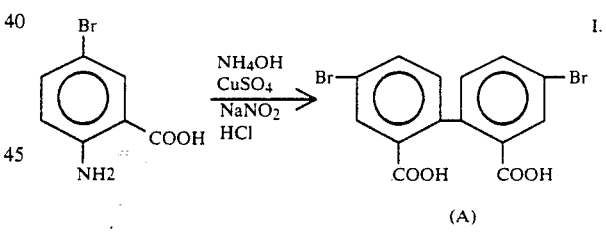

(A)

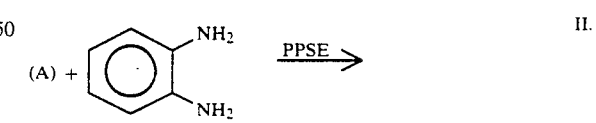

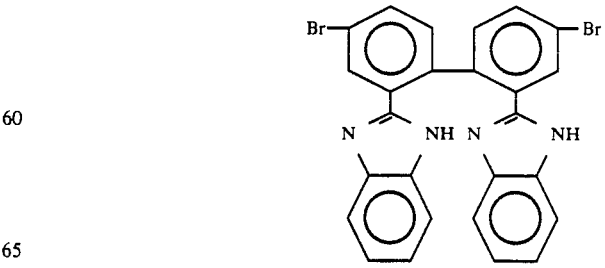

(B)

(B) $\xrightarrow{\text{CuCN}}{\text{NMP}}$ 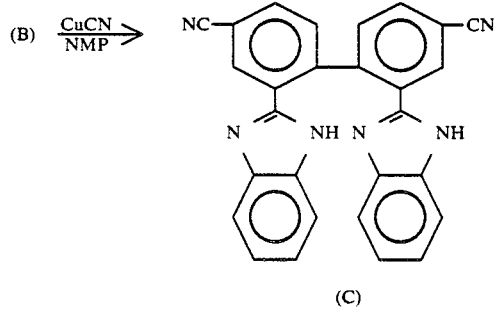 III.

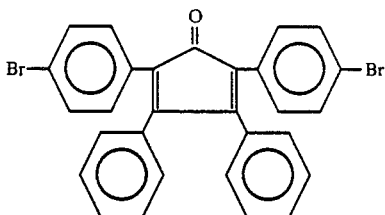

(C) $\xrightarrow{\text{H}_3\text{PO}_4}{\text{NMP}}$ 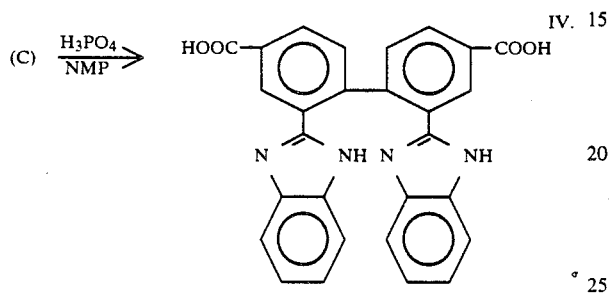 IV.

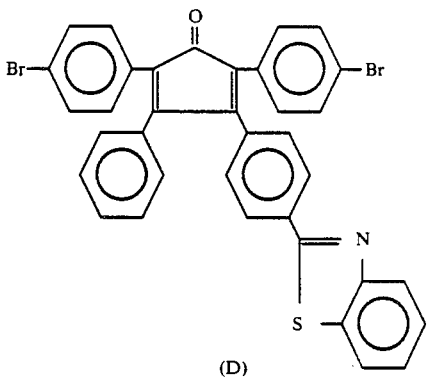

(D)

As shown by equation I above, 4,4'-dibromodiphenic acid is prepared by diazotizing 2-amino-5-bromobenzoic acid with sodium nitrate, followed by reduction with cuprous sulfate.

Equation II, above, illustrates the conversion of 4,4'-dibromodiphenic acid to 4,4'-dibromo-2,2'-bisbenzimidazolyl biphenyl. In this step, o-phenylenediamine is reacted with the 4,4'-dibromodiphenic acid in PPSE (trimethylsilyl polyphosphate) solution. The reaction is carried out at an elevated temperature, e.g., about 140° C.-180° C., for about 4 to 40 hours.

4,4'-Dibromo-2,2'-bisbenzimidazolyl biphenyl is converted to 4,4'-dicyano-2,2'-bisbenzimidazolyl biphenyl using CuCN, as shown in equation III. The reaction is carried out in a suitable solvent, such as N-methyl-2-pyrrolidinone, at a suitable temperature, such as at reflux of the solvent, for about 4 to 24 hours. The 4,4'-dicyano-2,2'-bisbenzimidazolyl biphenyl is then converted to 4,4'-dicarboxy-2,2'-bisbenzimidazolyl biphenyl by treating same with phosphoric acid, as shown in equation IV. The reaction is carried out in phosphoric acid at a temperature of about 140° C.-180° C., for about 4 to 24 hours.

4,4''-dicarboxy-2'-phenyl-3'-[2-(4-phenylbenzthiazole)]-6'-[2-(3-phenylbenzimidazole)]-p-terphenyl is prepared as shown by the following equations:

(D) + HC≡C— 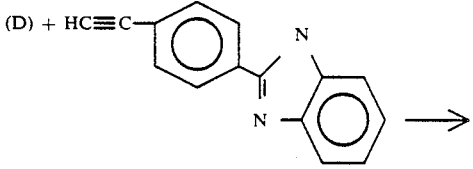 VI.

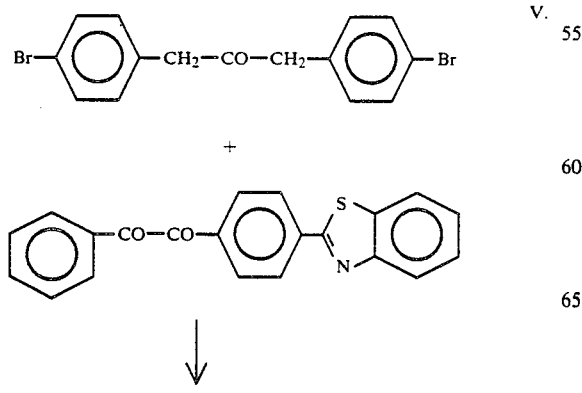 V.

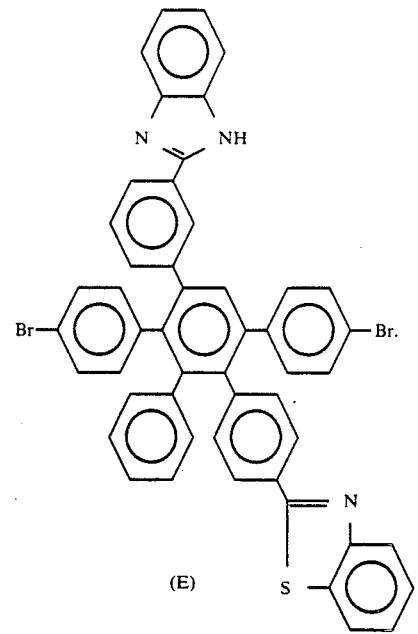

(E) $\xrightarrow{\text{1. CuCN}}{\text{2. H}_3\text{PO}_4}$ VII.

-continued

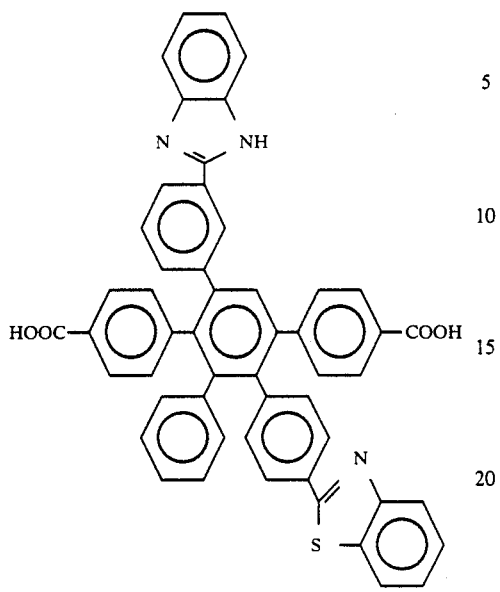

As shown by equation V, 4-benzthiazole benzil is reacted with 1,3-bis(p-bromophenyl)-2-propanone to form 2,5-bis(p-bromophenyl)3-phenyl-4-(2-phenylbenzthiazole) cyclopentadieneone (D). Substantially equimolar amounts of the benzil and the propanone are used. The reaction is carried out in the presence of an alkali metal hydroxide or an organoammonium hydroxide under reflux conditions in a suitable reaction medium. An alcohol, such as ethanol, propanol, butanol, or the like, can be conveniently used as the reaction medium. The amount of the hydroxide can vary within rather broad limits but generally ranges from about 0.1 to 0.75 mole per mole of the benzil. The reaction mixture is usually maintained under reflux condition for about 15 minutes to 8 hours.

In the second part of the synthesis, as shown by equation VI, the cyclopentadieneone (D) is reacted with 2-(3-ethynylphenyl) benzimidazole to form the dibromo terphenyl compound (E). In conducting the reaction, an excess of the acetylenic compound is used, e.g., about 1.5 to 10 moles per mole of the cyclopentadieneone. The reaction is carried out in a suitable reaction medium, such as a chlorinated hydrocarbon, under reflux conditions for about 15 minutes to 24 hours.

The third and fourth parts of the synthesis are shown combined as equation VII. The dibromo terphenyl compound (E) is first reacted with cuprous cyanide to form the corresponding dicyano terphenyl compound. A molar excess of cuprous cyanide, e.g., about 1.5 to 15 moles per mole of the dibromo terphenyl compound is used. The reaction is carried out in an inert atmosphere under reflux conditions, using a suitable reaction medium, such as N-methyl-2-pyrrolidinone. A reaction period of about 8 to 24 hours is usually sufficient to affect the substitution of the bromine atoms with cyano groups. The resulting dicyano terphenyl compound is hydrolyzed to provide the desired 4,4'''-dicarboxy-2'-phenyl-3'-[2-(4-phenylbenzthiazole)]-6'-[2-(3-phenylbenzimidazole)]-p-terphenyl. The reaction may be carried out in phosphoric acid at an elevated temperature of about 160° C. to 180° C. for about 1 to 8 hours.

The 2,5-bis(p-bromophenyl)-3-phenyl-4-(2-phenylbenzthiazole) cyclopentadieneone may be prepared by the procedures described by Arnold et al, U.S. Pat. No. 4,892,953, which is incorporated herein by reference.

The dicarboxylic acids of this invention are useful in preparing polymers having repeating units of the formula:

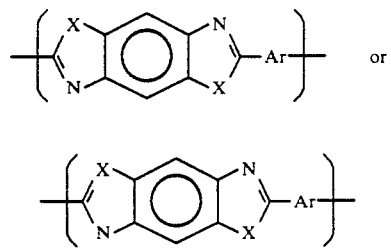

wherein X is —O—, —NH— or —S—, and wherein Ar is

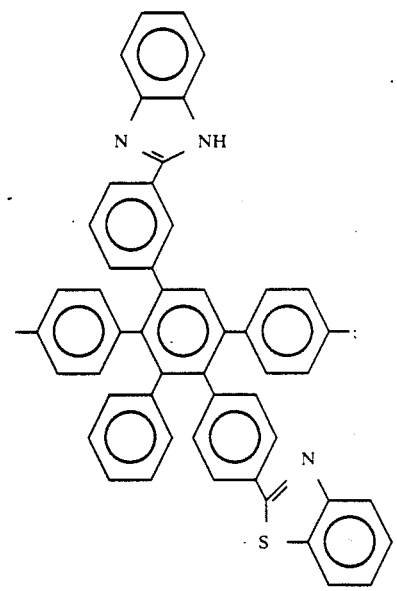

and copolymers having repeating units of the formula:

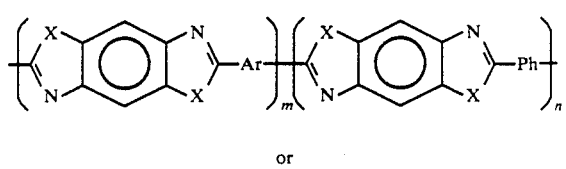

or

-continued

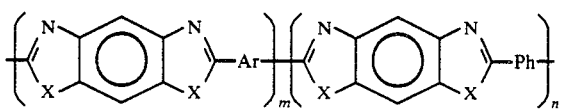

wherein X is —O—, —NH— or —S—, wherein Ph is 1,4-phenylene, wherein Ar is as described above, and wherein m is about 0.02 to 0.50 and n is 1.0 −m.

Preparation of these polymers and copolymers is described in copending applications Ser. Nos. 07/686,205 and 07/686,204, respectively, filed of even date herewith.

The following examples illustrate the invention:

EXAMPLE I

Synthesis of 2-Benzimidazole Terephthalic Acid

A solution of 19.21 g (0.1 mole) of trimellitic anhydride in 200 ml of dimethylformamide (DMF) was added to a solution of 10.81 g (0.1 mole) of o-phenylenediamine in 200 ml of DMF. The mixture was stirred for one hour at room temperature then heated to reflux for an additional hour. The solution was cooled to 25° C., during which time a precipitate formed. The solid was collected by suction filtration and washed several times with benzene Yield: 4.8 g of white crystals, mp 312° C.–314° C. Analysis calculated for $C_{21}H_{10}N_4S_2$: C, 65.95; H, 2.63; N, 14.65. Found: C, 64.89; H, 2.89, N, 14.40.

EXAMPLE II

4,4′-Dibromodiphenic acid

2-Amino-5-bromobenzoic acid (100 g, 0.116 mole), HCl (220 g) and water (300 ml) were ground in a mortar, then transferred to a 2-l round bottom flask fitted with a mechanical stirrer, thermometer and nitrogen purge. The slurry was cooled to <5° C. and a sodium nitrite solution (35.2 g, 0.512 mol in 400 ml water) was added slowly over a period of 30 minutes. The resulting diazonium salt solution was held below 5° C., then filtered immediately before use.

Cupric sulfate pentahydrate (161.6 g, 0.648 mol) was dissolved in 700 ml of water followed by addition of 280 ml of concentrated ammonium hydroxide. The solution was cooled to 10° C.

The cupric sulfate solution at <10° C. was added to a flask equipped with a mechanical stirrer and an addition funnel fitted with an upturned extension to permit addition of the diazonium salt solution below the surface of the reducing agent, without clogging.

Portions of the cold diazonium salt solution (approx. 50 ml each) were added dropwise (about 10 ml/minute) to the reducing solution maintained at 10° C. After the addition was complete, stirring was continued for several minutes. The resulting solution was then heated rapidly to boiling and acidified to pH 2 with concentrated HCl. A material precipitated as a light brown solid. After standing overnight, the solution was filtered and washed with water. The crude solid product was stirred in 400 ml of water and sodium bicarbonate was added. The resulting solution was filtered and acidified while hot with 6N HCl. The precipitate was washed with water and dried at reduced pressure at 100° C. Yield: 41.3 g (45%), mp 268° C.–269° C. The dark brown material was dissolved in 150 ml of ether and passed through a silica bed. Analysis by HPLC showed the presence of several impurities. To further purify the compound, the product was refluxed overnight in acetic anhydride to convert the diacid to the anhydride. When the solution was cooled, the anhydride crystallized as a white solid, which was recovered by filtration. The anhydride was hydrolyzed by reflux with 1N NaOH, then recovered by acidification of the aqueous filtrate. The subsequently dried material had a mp of 275° C.–276° C. The neutralization equivalent determined by potentiometric titration was found to be 196 (calcd. 200.1). Analysis calculated for $C_{14}H_8Br_2O_4$: C, 42.03; H, 2.01; Br, 39.95. Found: C, 39.35; H, 1.97, Br, 39.04.

Trimethylsilyl polyphosphate

Trimethylsilyl polyphosphate solution (PPSE) was prepared by adding 100 g $P_2O_5$ to 500 ml of 1,2-dichlorobenzene and 250 ml of hexamethyldisiloxane under nitrogen. This mixture was stirred and heated under reflux conditions for one hour, resulting in a clear solution. The solution was cooled and filtered.

4,4′-dibromo-2,2′-bisbenzimidazolyl biphenyl

To the PPSE solution was added 15.0 g of 4,4′-dibromodiphenic acid, 8.11 g of o-phenylene diamine (recrystallized from methylene chloride and charcoal). This mixture was rapidly heated to 160° C. and maintained there for 20 hours. The solution was cooled, then poured into 2 l of 10% $NaHCO_3$ solution. The product was filtered, washed with 300 ml of hot methylene chloride, then extracted using a Soxhlet extractor using 10% $NaHCO_3$ overnight. The product was dried then recrystallized from ethanol to give 11 g of white crystals, mp 326° C.–328° C. Analysis calculated for $C_{26}H_{16}N_4Br_2$: C, 57.38; H, 2.96; N, 10.29. Found: C, 57.81; H, 3.04, N, 10.30.

4,4′-dicyano-2,2′-bisbenzimidazolyl biphenyl

A mixture of 4,4′-dibromo-2,2 -bisbenzimidazolyl biphenyl (12.5 g, 0.023 mole), aqueous cuprous cyanide (6 g, 0.067 mole), and dry N-methyl-2-pyrrolidinone (125 ml) was heated under nitrogen to reflux for 18 hours. The reaction mixture was cooled, then poured into 300 ml water containing 30 g of NaCN. The resulting gray precipitate was washed with 100 ml of 10% aqueous NaCN, then with water, then dried in an oven at 100° C. The crude product was recrystallized from tetrahydrofuran/heptane (1:2) using activated charcoal, to give 8.4 g of white crystals, mp 347° C. –349° C. Analysis calculated for $C_{28}H_{16}N_6$: C, 77.05; H, 3.69; N, 19.25. Found: C, 76.90; H, 3.58, N, 19.46.

4,4′-dicarboxy-2,2′-bisbenzimidazolyl biphenyl

A solution of 8 g of 4,4′-dicyano-2,2′-bisbenzimidazolyl biphenyl (0.018 mole) and 150 g of 100% phosphoric acid was heated under nitrogen to 160° C. for 18 hours. The solution was cooled to 25° C., then poured into 1 l of water to precipitate a white solid. The solid was collected by filtration, washed with water and air dried. The product was purified by dissolving it in 10% aqueous sodium bicarbonate/charcoal, then precipitating the diacid product with glacial acetic acid. The product was filtered, washed with water and dried in a vacuum oven at 100° C. Yield: 7.4 g, mp >400° C. Analysis calculated for $C_{28}H_{18}N_4O_4$: C, 70.88; H, 3.83; N, 11.81. Found: C, 70.25; H, 3.96, N, 11.46.

Preparation of 4,4'-dibromo-2,2'-bisbenzimidazolyl biphenyl by prior art method To a mixture containing 3.0 g of 4,4'-dibromodiphenic acid and 1.8 g of o-phenylene diamine was added 100 g of polyphosphoric acid (85%). The mixture was stirred and heated at 60° C. for 1 hour, 100° C. for 1 hour, and finally at 160° C. for 24 hours. The cooled heterogenous mixture was poured into 2L of distilled water. The procedure was not successful in that the product was identified as an anhydride (IR, MS and elemental analysis). This procedure was repeated using methanesulfonic acid/phosphorus pentoxide and polyphosphoric acid/sulfolane as solvents. The same result was obtained.

EXAMPLE III

Synthesis of 4,4''-dicarboxy-2'-phenyl-3'-2-(4-phenyl-benzothiazole)]-6'-[2-(3-phenylbenzimidazole)]-p-terphenyl

2-I3-ethynylphenyl)benzimidazole

A solution of 4-(3-phenyl-2-benzimidazole)-2-methyl-3-butyn-2-ol (20 g, 0.076 mol) in 600 ml toluene was formed with heating under nitrogen. A 5% methanolic KOH solution (15 ml) was added and the mixture stirred and heated under reflux for 3 hours. Acetone formed as the reaction progressed and was removed by azeotropic distillation with toluene. The mixture was filtered through silica gel and removed under pressure. The resulting yellow solid was recrystallized from ethanol/water (50:50) to give 14 g of light yellow crystals. Analysis calculated for $C_{15}H_{10}N_2$: C, 82.55; H, 4.62; N, 12.83. Found: C, 82.40; H, 4.71, N, 12.86.

4,4''-dibromo-2'-phenyl-3'-[2-(4-phenyl-benzothiazole)]-6'-[2-(3-phenylbenzimidazole)]-p-terphenyl A mixture of 2-(3-ethynylphenyl)benzimidazole (13.1 g, 0.06 mol), 2,5-bis(p-bromophenyl)-3-phenyl-4-(2-phenylbenzthiazole) cyclopentadienone (32 g, 0.047 mol) and 200 ml of 1,2,4-trichlorobenzene was refluxed under a nitrogen atmosphere for 120 hours. After cooling to 25° C., the solution was precipitated by pouring into 3 liters of petroleum ether to give a light yellow solid which was collected by filtration and dried at 100° C. The product was recrystallized from methylene chloride/heptane to give 20 g of light yellow product, mp >340° C. Analysis calculated for $C_{50}H_{31}N_3SBr_2$: C, 69.37; H, 3.61; N, 4.85. Found: C, 68.93; H, 3.75, N, 4.75.

4,4''-dicyano-2'-phenyl-3'-[2-(4-phenyl-benzothiazole)]-6-[2-(3-phenylbenzimidazole)1-p-terphenyl A mixture of 15 g of 4,4''-dibromo-2'-phenyl-3'-[2-(4-phenyl-benzothiazole)]-6'-[2-(3-phenylbenzimidazole)]-p-terphenyl (0.017 mole), 45 g CuCN (0.5 mole) and 300 ml dry N-methyl-2-pyrrolidinone was refluxed under nitrogen for 18 hours. After cooling, the mixture was poured into 1 l of water containing 100g NaCN. The resulting gray precipitate was washed with 10% aqueous NaCN and oven dried at 100° C. The crude product was dissolved in methylene chloride, passed through a silica gel column and eluted with methylene chloride. Removal of the solvent under reduced pressure gave 10.5 g, mp >340° C. Analysis calculated for $C_{52}H_{31}N_5S$: C, 82.41; H, 4.12; N, 9.25. Found: C, 82.16; H, 4.20, N, 9.36.

4,4''dicarboxy-2'-phenyl-3'-[2-(4-phenyl-benzothiazole)]-6'-[2-(3-phenylbenzimidazole)]-p-terphenyl A mixture of 10 g of 4,4''-dicyano-2'-phenyl-3'-[2-(4-phenyl-benzothiazole)]-6'-[2-(3-phenylbenzimidazole)]-p-terphenyl (0.013 mole) and 500 g of phosphoric acid was heated under nitrogen at 160° C. for 4 hours. After cooling, the mixture was poured into 3.5 l of water. The resulting precipitate was washed with water and oven dried at 100° C. The crude product was recrystallized from heptane/methylene chloride to give 8.7 g, mp >340° C. Analysis calculated for $C_{52}H_{33}N_3O_4S$: C, 78.47; H, 4.18; N, 5.28. Found: C, 78.98; H, 4.44, N, 5.29.

Various modifications may be made to the invention as described without departing from the spirit of the invention or the scope of the appended claims.

We claim:
1. 2-Benzimidazole terephthalic acid.
2. 4,4'-Dicarboxy-2,2'-bisbenzimidazole biphenyl.
3. 4,4''-Dicarboxy-2'-phenyl-3'-[2-(4-phenylbenzthiazole)]-6'-[2-(3-phenylbenzimidazole)]-p-terphenyl.

* * * * *

UNITED STATES PATENT AND TRADEMARK OFFICE
CERTIFICATE OF CORRECTION

PATENT NO. : 5,081,256
DATED : January 14, 1992
INVENTOR(S) : Fred E. Arnold et al It is certified that error appears in the above-identified patent and that said Letters Patent is hereby corrected as shown below:

Cover page, item [75], insert the name and address of inventor 3, --Thuy D. Dang, Dayton, Ohio--.
   Col 6  line 15, change "X" to --N--.
   Col 6, line 17, change "N" to --X--.
   Col 7, line 27, insert a period after "benzene".
   Col 9, line 19, after "phenyl-3'-", insert --[--.
   Col 9, line 21, after "2-", change "I" to --(--.
   Col 10, line 7, after "phenylbenzimidazole)", change "1" to --]--.

Signed and Sealed this

Twentieth Day of April, 1993

*Attest:*

MICHAEL K. KIRK

*Attesting Officer*      *Acting Commissioner of Patents and Trademarks*